United States Patent [19]

Schultz et al.

[11] Patent Number: 5,034,473
[45] Date of Patent: Jul. 23, 1991

[54] COMPOSITION OF POLYEPOXIDE DERIVED FROM ALKOXY-SUBSTITUTED ALLYLPHENOL AND CARBOXY-TERMINATED POLYESTER OR POLYAMIDE

[75] Inventors: Rose A. Schultz, Princeton; S. Steve Chen, Belle Mead, both of N.J.

[73] Assignee: National Starch and Chemical Investment Holding Company, Wilmington, Del.

[21] Appl. No.: 394,900

[22] Filed: Aug. 17, 1989

[51] Int. Cl.$^5$ .................. C08L 67/02; C08L 77/06
[52] U.S. Cl. .................... 525/423; 525/438
[58] Field of Search ................ 525/438, 423

[56] References Cited

U.S. PATENT DOCUMENTS

| | | | |
|---|---|---|---|
| 2,965,607 | 12/1960 | Martin et al. | 528/112 |
| 3,576,903 | 4/1971 | Groff | 525/423 |
| 3,739,041 | 6/1973 | Schmid et al. | 260/835 |
| 4,557,860 | 12/1985 | DiSalvo et al. | 252/512 |
| 4,668,736 | 5/1987 | Robins et al. | 525/65 |

FOREIGN PATENT DOCUMENTS 0866410 4/1961 United Kingdom ............... 525/438

*Primary Examiner*—John C. Bleutge
*Assistant Examiner*—Robert E. L. Sellers, II
*Attorney, Agent, or Firm*—Eugene Zagarella, Jr.; Edwin M. Szala

[57] ABSTRACT

Epoxy compositions having improved toughness and flexibility comprising a polyepoxide of the formula

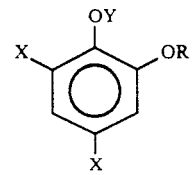

wherein each X is H, allyl or glycidyl, Y is allyl or glycidyl and R is an alkyl of 1 to 4 carbons with there being at least two epoxy groups on the ring modified with a carboxy terminated polymer.

16 Claims, No Drawings

1

COMPOSITION OF POLYEPOXIDE DERIVED FROM ALKOXY-SUBSTITUTED ALLYLPHENOL AND CARBOXY-TERMINATED POLYESTER OR POLYAMIDE

BACKGROUND OF THE INVENTION

This invention relates to epoxide formulations comprising polyfunctional epoxides which are modified with selected carboxy terminated polymers to give a composition with improved toughness and flexibility.

Epoxy resins have gained wide acceptance for their use in adhesives and in other applications because of the variety of properties they possess including good mechanical and thermal properties, outstanding adhesion to various substrates, high chemical and corrosion resistance, low shrinkage upon cure, flexibility, good electrical properties and the ability to be processed under varied conditions. The many properties possessed by epoxies, as well as the ability to change or modify these properties through formulation additives, make them very versatile and especially useful in a number of adhesive applications.

Many different epoxy resins are known in the art, as well as formulations containing these materials for diverse applications. Typical epoxy resins and formulations are disclosed in "Handbook of Thermoset Plastics", edited by Sidney H. Goodman, Noyes Publications, pp. 132-182, 1986; "Adhesives Technology Handbook", Arthur H. Landrock, Noyes Publications, pp 144-153, 1985; and in Encyclopedia of Polymer Science and Technology, Vol. 6, pp. 322-382, 1986.

While the known epoxy resins and the different formulations for such resins have provided great versatility in their application, the need exists for an epoxy adhesive which will provide better toughness and flexibility properties.

SUMMARY OF THE INVENTION

The present invention provides epoxy compositions having improved toughness and flexibility properties and which comprise a polyfunctional epoxide and a carboxy terminated polymer modifier.

More particularly, this invention is directed to compositions comprising a polyepoxide of the formula:

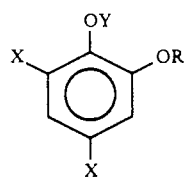

wherein each X is H, allyl or glycidyl, Y is allyl or glycidyl and R is lower alkyl of 1 to 4 carbons with there being at least two epoxy groups on the ring, and a carboxy terminated polymer modifier of the general formula:

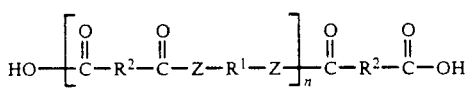

wherein $R^1$ is a linear hydrocarbon having ether linkages or linear hydrocarbons substituted with sulfone, sulfide, phosphorous oxide, silane or siloxane, $R^2$ is a $C_{2-20}$ straight or branched chain or cyclic saturated or unsaturated hydrocarbon, Z is O, NH or $NR^3$ $R^3$ is $C_{1-10}$ alkyl, alkenyl or aryl and n is at least 1.

DETAILED DESCRIPTION OF THE INVENTION

The polyfunctional epoxides used in this invention can be prepared by reacting the appropriate substituted phenol with epihalohydrin followed by dehydrohalogenation or by the direct epoxidation of an ethylenically unsaturated group by oxidation with a peracid or by a combination of such methods. This is exemplified by the following reaction where eugenol, i.e., [2-methoxy-4-(2-propenyl)]phenol is reacted with epichlorohydrin followed by the oxidation with peracetic to obtain eugenol dioxide i.e., [(2-methoxy-4-oxiranylmethyl phenoxy)-methyl]oxirane:

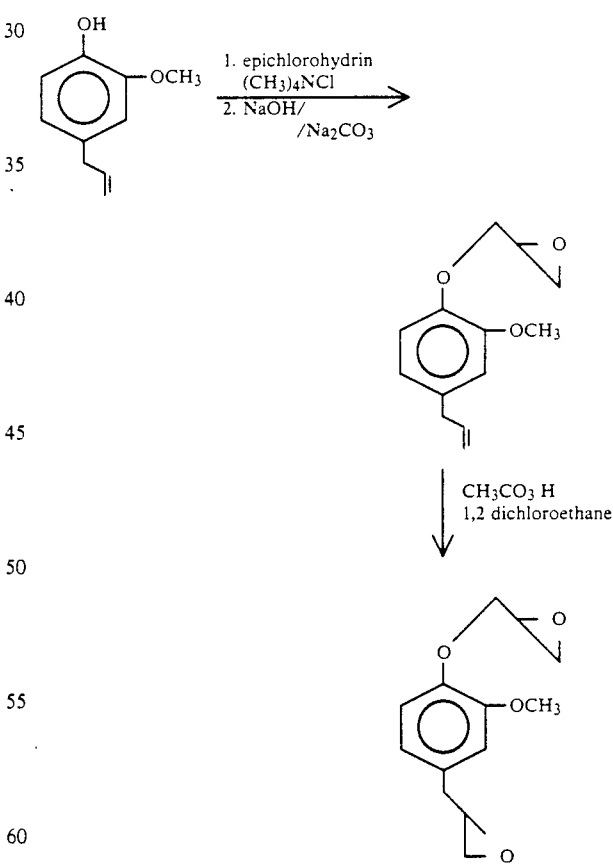

The epoxides can also be prepared by other known techniques and may include the Claisen rearrangement of allylic groups in the formation thereof. These polyfunctional epoxides have the following general formula:

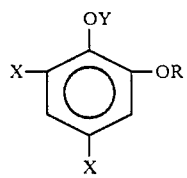

wherein each X is H, allyl or glycidyl, Y is allyl or glycidyl and R is lower alkyl of 1 to 4 carbon atoms with the proviso that there is at least two epoxy groups on the ring. Preferably, X will be H or glycidyl, Y is glycidyl and R is methyl.

The epoxy compositions of this invention comprise the polyepoxides (I) noted above and also a modifier which is a carboxy terminated polymer that is the reaction product of a polymeric diol, polyol, or diamine with a cyclic dianhydride.

The carboxy terminated polymers which are especially useful are those having the following formula:

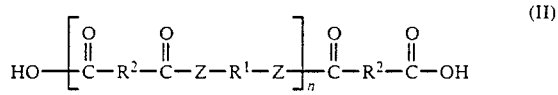

wherein $R^1$ is a linear hydrocarbon having ether linkages or linear hydrocarbons substituted with sulfone, sulfide, phosphonate, phosphine oxide, silane or siloxane, $R^2$ is a $C_{2-20}$ straight or branched chain or cyclic saturated or unsaturated aliphatic or aromatic hydrocarbon, Z is O, NH or $NR^3$; where $R^3$ is $C_{1-10}$ alkyl, alkenyl or aryl and n is at least 1.

Preferred carboxy terminated polymer modifiers (II) used in this invention are those where $R^1$ is a linear hydrocarbon having ether linkages. Also preferred are modifiers (II) wherein $R^2$ is a residue of the cyclic anhydride, n is 1 and Z is O.

Suitable polyethers to obtain the linear polyethers in formula (II) are those having a molecular weight of about 500 to 5000 obtained by removal of hydroxyl groups from an oligomeric polyol. Preferred polyethers have a molecular weight of about 650 to 2500 and more preferably about 1000-2200. Particularly suitable polyethers are those obtained from polypropylene glycol having the structure:

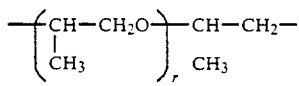

where r is at least 8 and those obtained from polytetramethylene glycol having the structure:

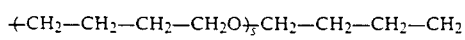

where s is at least 7.

The carboxy terminated polymer modifiers (II) are preferably formed by the reaction of oligomeric polyols, preferably diols such as polyethylene glycol, polypropylene glycol, polytetramethylene glycol or copolymers thereof, with cyclic anhydrides, preferably succinic anhydride or phthalic anhydride. Also useful in forming the carboxy terminated polymers (II) are amine terminated polymers in place of the polyols.

In actual practice, the modifier is formed by reacting the polyol with the anhydride in a solvent in which both are soluble at an appropriate temperature (optionally in the presence of a catalyst such as a tertiary amine) to assure formation of the product. Appropriate solvents include organic solvents, for example, toluene and tetrahydrofuran. The solvent is then removed by any convenient means, preferably vacuum distillation.

The epoxide formulation is prepared by admixing the polyepoxides with an effective amount of the carboxy terminated polymer modifiers and more particularly, the amount of modifier will be at a concentration ranging from about 1 to 99 parts per hundred parts of epoxide by weight, preferably from about 2 to 75 and more preferably about 5 to 50 parts per hundred parts of epoxide by weight.

The modified epoxides are admixed with a curing agent and other additives and modifying materials as desired. Suitable curing agents which are conventionally known and used in effective curing amounts are aliphatic and aromatic amines and polyamines, aminopolyamides and phenolic novolacs. Optionally catalysts which catalyze the curing agent or the polymerization of the epoxide (thereby shortening the cure time) can be used in the composition. Typical catalysts include substituted ureas, substituted imidazoles, tertiary amines, triphenyl phosphine and quaternary phosphonium salts.

In many cases, especially when amine curing agents are used, it is also desirable to pre-react the carboxy terminated polymer modifier with the epoxide to assure that the modifier is fully reacted after cure. This pre-reaction is accomplished by heating the modifier with the epoxide compound to a temperature of about 125° to 200° C. for 1 to 2 hours in the presence of a catalyst until all the carboxyl groups are reacted. The reaction can be monitored by the disappearance of carboxyl groups by any convenient method.

Various additive and modifying material may be included in the epoxy composition of this invention. These include fillers such as electrically and thermally conductive fillers, colorants and dyes, viscosity modifiers, adhesion promotors, diluents, reinforcing fibers, etc.

The modified epoxy compositions of this invention are particularly useful in adhesive compositions, in electrical/electronic applications such as in circuit boards, in composites and other molded products and as coatings including encapsulation coatings.

The following examples serve to illustrate further the embodiments of the invention and are not intended to be construed as limitations thereof. In the examples, all parts and percentages are given by weight and all temperatures in degrees Celsius unless otherwise noted.

EXAMPLE I

This example illustrates the preparation of eugenol diepoxide, i.e., [(2-methoxy-4-oxiranylmethyl phenoxy)methyl]oxirane.

A multi-necked round bottom flask equipped with mechanical stirrer, thermometer and a reflux condenser was charged with 20 g (0.122 mole) of eugenol, 22.6 g (0.244 mole) of epichlorohydrin and a catalytic amount (0.22 g) of tetramethyl ammonium chloride. The reaction mixture was heated at 90°–95° C. for nine hours at which point the reaction was judged to be complete by gas chromatographic analysis. The vessel was cooled to 10° C. and a slurry of 26 ml (0.120 moles) 5N NaOH saturated with $Na_2CO_3$ was added and stirred at room temperature for four hours until the reaction was complete (gas chromatographic analysis). The phases were separated and the aqueous layer washed with $CHCl_3$. The organic layers were combined and washed with water until the water wash was pH neutral. The organic layer was dried over $MgSO_4$, filtered and the solvent and residual epichlorohydrin removed under aspirator vacuum. The residual oil was distilled at 130°-135° C./3 mm Hg on a Kugelrohr apparatus to yield 19.7 g (73%) of a clear colorless oil ([2-methoxy-4-(2-propenyl)-phenoxy]methyl)oxirane which solidified on cooling (m.p. 25°-30° C.) and had a titratable epoxy equivalent weight of 219 (theoretical equivalent weight is 220).

The allyl compound prepared above (10 g, 0.045 mole) was charged into a round bottom flask equipped with magnetic stirrer and nitrogen purge, along with 50 ml of dichloroethane and 2 g of sodium acetate. The reaction vessel was cooled to 5° C. and 21.7 g (0.1 mole) of peracetic acid (35 wt. % in acetic acid) was added and stirred for 48 hours at room temperature. The mixture was washed with water (150 ml), 5% $Na_2SO_3$ (100 ml), 5% $NaHCO_3$ (100 ml), and water again (50 ml). The organic layer was dried over $MgSO_4$, filtered and the solvent removed in vacuo. The residual oil was distilled at 150° C./3 mm Hg on a Kugelrohr apparatus to yield 6.3 g (59%) of a pale yellow oil [(2-methoxy-4-oxiranylmethyl phenoxy)methyl]oxirane i.e. eugenol diepoxide, which solidified on cooling (m.p. 40°-53° C.) and had an epoxy equivalent weight of 134. After recrystallization from 2-propanol, the material was isolated as a white solid (m.p. 63°-65° C.) with an epoxy equivalent weight of 123.

Analysis:

IR (neat, melt); 1590 $cm^{-1}$ (phenyl, m); 1140 $cm^{-1}$ (c-o-c, m).

$^1$H NMR ($CDCl_3$): 2.7 ppm (m, 6H, Ar-C$\underline{H}_2$

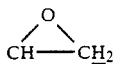

and OC$\underline{H}_2$

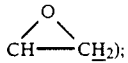

3.2 ppm (m, 2H,

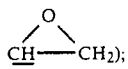

3.9 ppm (s, 3H, OC$\underline{H}_3$); 4.2 ppm (m, 2H, OC$\underline{H}_2$

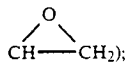

6.9 ppm (m, 3H, Ar-H).

EXAMPLE II

This example illustrates the preparation of the triepoxide of eugenol, i.e. [[2-methoxy-4,6-di(oxiranylmethyl)phenoxy]methyl]oxirane.

A multi-necked round bottom flask equipped with mechanical stirrer, thermometer, reflux condenser and dropping funnel was charged with 150 g of eugenol, 400 ml of 2-propanol and a gentle flow of $N_2$ was introduced. A 40% NaOH solution (43.9 g NaOH, 1.1 mole in 66 g $H_2O$) was added slowly to the externally cooled reaction vessel at a rate to maintain the internal temperature below 35° C. The mixture was stirred for 10 minutes and 113 ml (1.38 mole) of allyl chloride was added to the flask and heated to maintain a gentle reflux for 1 hour, at which time the reaction was complete (GC analysis). The flask was charged with 300 ml water. A Dean-Stark Trap and steam bath were used to azeotropically remove the 2-propanol. The distillation ceased when the temperature reached 94° C. and after cooling, 300 ml of hexane was added and the water layer separated. The organic layer was washed with water until the pH of the water wash was neutral, the layer was then dried over $MgSO_4$, filtered and the solvent removed under vacuum. The product was vacuum distilled to yield 155 g (84%) of a pale yellow 3-[2-methoxy-4-(2-propenyl)phenoxy]propene.

This product (155 g) was then charged to a round bottom flask which was mechanically stirred and heated with an oil bath under nitrogen purge. The internal temperature was held at 190°-200° C. for 2.5 hours when the reaction was complete (GC analysis) and a dark oil, 2-methoxy-4,6-di-(2-propenyl)phenol was recovered (147 g, 95%).

The methoxy dipropenyl phenol prepared above was then charged (25 g, 0.122 mole) into a multi-necked round bottom flask equipped with mechanical stirrer, thermometer and reflux condenser. Epichlorohydrin (22.65 g, 0.245 mole) was added along with a catalytic amount (0.23 g) of tetramethylammonium chloride. The mixture was heated at 90°-95° C. for 33 hours and then the vessel was cooled to 10° C. and a slurry of 26 ml 5N NaOH (0.238 moles) saturated with $Na_2CO_3$ was added and stirred at room termperature until reaction was complete (GC analysis) after about 48 hours. The phases were separated and the aqueous layer washed with $CHCl_3$ (2×50 ml). The organic layers were combined and washed with water until the pH of the water wash was neutral. The organic layer was than dried over $MgSO_4$, filtered and the solvent and residual epichlorohydrin removed under aspirator vacuum. The residual oil was distilled on a Kugelrohr apparatus (130°-40° C./3 mm Hg) to yield 23.7 g (74%) of a clear pale yellow oil, ([2-methoxy-4,6-di-(2-propenyl)phenoxy]methyl)oxirane.

This allylic product prepared above was charged (10 g, 0.38 mole) with 50 ml of dichloroethane and 3.6 g of sodium acetate into a round-bottom flask. The vessel was cooled to 5° C. and 36.3 g (0.167 mole, 35 wt % in acetic acid) of peracetic acid was added and stirred for 48 hours at room temperature. The mixture was transferred to a separatory funnel and separated. The organic layer was washed with 150 ml water, 200 ml of $NaHCO_3$ (5%) and another 100 ml water and then dried over $MgSO_4$, filtered and the solvent removed in vacuum. The product was distilled on a Kugelrohr apparatus (180° C./3 mm Hg) to yield 4.2 g (38%) of a clear yellow oil [[2-methoxy-4,6-di-(oxiranyl methyl)phenoxy]-methyl]oxirane having an epoxy equivalent weight of 118 (theoretical 97).

Analysis:

IR (neat): 1590 cm$^{-1}$ (phenyl, m); 1100 cm$^{-1}$ (c-o-c, m); absorbances at 3470 cm$^{-1}$ and 1730 cm$^{-1}$ suggest the formation of some hydroxy acetate.

$^1$H NMR (CDCl$_3$): 2.7 ppm (m, 10H, Ar-C$\underline{H}_2$

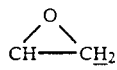

and OC$\underline{H}_2$

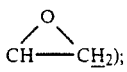

3.3 ppm (m, 3H,

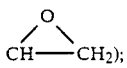

3.9 ppm (s, 3H, OC$\underline{H}_3$); 4.2 ppm (m, 2H, OC$\underline{H}_2$

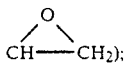

6.9 ppm (m, 3H, Ar-H).

EXAMPLE III

This example represents the synthesis of a typical carboxy terminated polyether modifier polymer.

A 3-liter, 4-neck round bottom flask equipped with condenser, thermometer, mechanical stirrer and nitrogen inlet was charged with 990.2 g of Terathane 1000 [DuPont, poly(oxytetramethylene)glycol having MW of 1000], 200.2 g of succinic anhydride and 150 ml. of toluene. The reaction mixture was heated to reflux for four hours (reflux temperature 160° C.). After the reaction was complete, the mixture was transferred to a one-neck round bottom flask and the volatiles were removed on a rotary evaporator under high vacuum. Yield of this clear, viscous resin was 99% and the neutralization equivalent determined by titration was 618 (theoretical 590).

EXAMPLE IV

This example shows the modification of eugenol diepoxide prepared in Example I with the carboxy terminated polymer prepared in Example III.

The epoxide of Example I, 15 g of eugenol diepoxide was combined with 6 g of the carboxy terminated polyether polymer of Example III and 0.1 g of triphenylphosphine, then mixed in a reactor and heated at 175° C. for one hour. After the mixture was cooled to room temperature, 9.4 g of a curing agent 4,4-diamino diphenyl sulfone (DDS) was dispersed into it by mixing. After curing, the T-peel strength of the product on a steel strip, was determined on an Instron Tester using the procedure described in ASTM D1876-72 and found to be 20 pli (pounds/linear inch).

EXAMPLE V

This example shows the modification of eugenol triepoxide prepared in Example II with the carboxy terminated polymer prepared in Example III.

The epoxide of Example II, 20 g of eugenol triepoxide was combined with 5.0 g of the carboxy terminated polyether polymer of Example III and 2.1 g of a phenol novolac curing agent along with 0.3 g of a proprietary substituted urea catalyst, and thoroughly mixed. After curing, the T-peel strength of the product on steel strips was determined on an Instron Tester using the procedure described in ASTM D1876-72 and found to be 3.3 pli (pounds/linear inch).

EXAMPLE VI

For comparative purposes, a different epoxide, 2-glycidylphenyl glycidyl ether (20 g) was modified in the same manner using 8 g of the same carboxy terminated polyether i.e. the one prepared in Example III. The combined mixture was pre-reacted in the presence of 0.1 g of triphenylphosphine at 175° C. for one hour and the product mixed with 11.7 g of the DDS curing agent. The T-peel strength of the product on a steel strip was determined in the same manner and found to be 1 pli (pounds/linear inch).

Also for comparative purposes, using 4 g of a carboxy terminated polybutadiene-acrylonitrile polymer (Hycar CTBN 1300×13, trademark of B. F. Goodrich) instead of the carboxy terminated polyether polymer of Example III, eugenol diepoxide (15 g) was modified in the same manner using 0.1 g of triphenylphosphine and 9.4 g of the DDS curing agent. The T-peel strength of the product on a steel strip was determined in the same manner and found to be 0.5 pli (pounds/linear inch).

The results show the improved toughness qualities of the modified epoxide product of this invention as compared with different epoxy products.

What is claimed is:

1. An epoxy composition having improved toughness and flexibility comprising a polyepoxide of the formula:

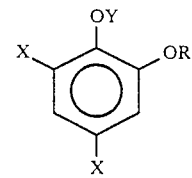

wherein each X is H, allyl or glycidyl, Y is allyl or glycidyl and R is an alkyl of 1 to 4 carbons with the proviso there is at least two epoxy groups on the ring and an effective amount of a carboxy-terminated polymer having the formula:

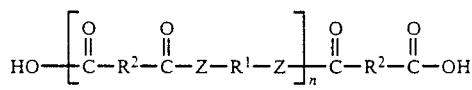

wherein R$^1$ is a linear hydrocarbon having ether linkages,

R$^2$ is a C$_{2-20}$ straight or branched chain or cyclic saturated or unsaturated hydrocarbon, Z is O or NH and n is at least 1.

2. The epoxy composition of claim 1 wherein each X is H or glycidyl, Y is glycidyl and R is methyl.

3. The composition of claim 2 wherein each X is glycidyl.

4. The composition of claim 2 wherein the polyepoxide is [(2-methoxy-4-oxiranylmethyl phenoxy)methyl]oxirane.

5. The epoxy composition of claim 2 wherein Z is O and n is 1.

6. The epoxy composition of claim 5 wherein the carboxy terminated polymer is present in an amount of from about 1 to 99 parts per hundred parts of the polyepoxide by weight.

7. The epoxy composition of claim 1 wherein the carboxy terminated polymer is present in an amount of from about 1 to 99 parts per hundred parts of the polyepoxide by weight.

8. The epoxy composition of claim 7 wherein each X is H or glycidyl, Y is glycidyl and R is methyl.

9. The epoxy composition of claim 7 wherein Z is O and n is 1.

10. The epoxy composition of claim 7 wherein about 2 to 75 parts of the carboxy terminated polymer are used per hundred parts of the polyepoxide by weight.

11. The epoxy composition of claim 10 wherein each X is H or glycidyl, Y is glycidyl and R is methyl.

12. The composition of claim 11 wherein Z is O and n is 1.

13. The composition of claim 12 wherein each X is glycidyl.

14. The composition of claim 13 wherein the polyepoxide is [(2-methoxy-4-oxiranylmethylphenoxy)methyl]oxirane.

15. The composition of claim 14 wherein about 5 to 50 parts of carboxy terminated polymer are used per hundred parts of polyepoxide by weight.

16. An adhesive composition containing the epoxy composition of claim 1.

* * * * *